United States Patent [19]
Van as

[11] Patent Number: 4,862,080
[45] Date of Patent: Aug. 29, 1989

[54] METHOD OF DERIVING A SPIN RESONANCE SIGNAL FROM A MOVING FLUID, AND DEVICE FOR PERFORMING THIS METHOD

[75] Inventor: Hendrik Van as, Lunteren, Netherlands

[73] Assignee: U.S. Philips Corporation, New York, N.Y.

[21] Appl. No.: 170,480

[22] Filed: Mar. 21, 1988

[30] Foreign Application Priority Data

Mar. 25, 1987 [NL] Netherlands ......................... 8700700

[51] Int. Cl.$^4$ ........................................... G01R 33/20
[52] U.S. Cl. ..................................... 324/306; 324/300
[58] Field of Search ................ 128/653; 324/300, 307, 324/306, 309

[56] References Cited

U.S. PATENT DOCUMENTS 4,654,591 3/1987 Moran .................................. 324/306

*Primary Examiner*—Michael J. Tokar
*Attorney, Agent, or Firm*—Algy Tamoshunas; Leroy Eason

[57] ABSTRACT

Method and apparatus for deriving flow information from magnetic resonance signals. A magnetic field gradient extends in the direction of the flow to make the magnetic resonance signals flow sensitive. In order to reduce the effect of relaxation times on the flow information an additional magnetic field component—a gradient or an r.f. signal—is applied which artificially reduces the relaxation times.

19 Claims, 5 Drawing Sheets

$v_a < v_b < \cdots < v_h$　　FIG. 4a $v_a < v_b < \cdots < v_h$

METHOD OF DERIVING A SPIN RESONANCE SIGNAL FROM A MOVING FLUID, AND DEVICE FOR PERFORMING THIS METHOD

BACKGROUND OF THE INVENTION

1. Field of the Invention

The invention relates to a method of deriving a spin resonance signal from a moving fluid which is subjected to a magnetic field consisting of a constant field component, one or more gradient field components, at least one of which extends in the direction of motion of the fluid, and a magnetic field component which is generated by r.f. electromagnetic signals perpendicularly to the constant field component in order to excite the nuclear spins of the fluid. The invention also relates to a device for performing the method.

2. Description of Related Art

A method of this kind is known inter alia from "Flow Imaging by Nuclear Magnetic Resonance", Van As et al, "Annales de Radiologie", Vol. 27, No. 5, 1984, pp. 405–413, and "The Study of Flow by Pulsed Nuclear Magnetic Resonance. II Measurement of Flow Velocities Using a Repetitive Pulse Method", Hemminga M. A. and de Jager P. A., "Journal of Magnetic Resonance", No. 37, 1980, pp. 1–16.

The state of the art method enables non-invasive determination of the velocity of a continuously or non-continuously moving fluid, possibly in the presence of an excess of stationary fluid in the immediate vicinity of the moving fluid. In this context a moving fluid is to be understood to mean a fluid flowing in an object, a stationary fluid in a moving object, or combinations of both.

According to the known method, the object in which the fluid is present is arranged between the poles of a magnet and is enclosed by a wire coil whereby the fluid is subjected to a series of brief r.f. electromagnetic pulses of equal duration. Moreover, a magnetic field gradient which extends in the direction of motion is applied.

In the state of equilibrium, in the absence of a magnetic field component generated by the r.f. electromagnetic pulses, the individual nuclear spins in the fluid perform a precessional motion around the constant magnetic field component. Using the r.f. magnetic field component, the nuclear spins can be excited so that they are rotated with respect to the constant field component. During the interval between the successive r.f. pulses the nuclear spins fan out and tend to resume the direction of the constant field component. Inter alia the linear and the volumetric flow rate of the fluid can be determined from the shape of the electric signals then generated in the wire coil. After calibration, each of said quantities can be measured in an absolute sense.

This known method has the drawback that the calibration curves for the relationship between the flow quantities and the measured signal depend greatly on the flow profile, and also that these calibration curves are determined to a high degree by the spin-spin and spin-lattice relaxation times of the fluid to be measured. The spin-spin relaxation time is a measure of the speed at which the nuclear spins fan out with respect to one another, the spin lattice relaxation time being a measure of the speed at which the nuclear spins return in the direction of the constant field component. In biological materials, notably the spin-spin relaxation time may be dependent on a large number of factors and may vary strongly, thus introducing a high degree of uncertainty in the interpretation of the measured signals so that comparatively large measurement errors may arise.

The effect of the spin-spin relaxation time on the measurement results can essentially be considered as the effect of a low-pass filter. In the case of a fluid whose flow varies in time and/or in an object whose motion varies in time, this filter effect distorts the measured signal, so that reliable and accurate measurements of the spin-spin relaxation time and the flow properties are not possible. In the case of imaging by means of the nuclear spin resonance technique, the spin-spin relaxation time has an adverse effect on the resolution of the images formed.

SUMMARY OF THE INVENTION

The invention aims to control the effect of the spin-spin relaxation time on the spin resonance signal generated in order to achieve an as accurate as possible measurment of the motion of fluids having a movement component which varies continuously and/or in time, and to form high-quality images. This is achieved in accordance with the invention in that the fluid is subjected to at least one further magnetic field component in such a manner that the excited nuclear spins relax in a manner imposed by said at least one further magnetic field component.

Notably the spin-spin relaxation time observed is artificially reduced in the method in accordance with the invention, so that it is no longer determined by the properties of the fluid to be measured but rather by the way in which the nuclear spins relax.

The major advantages of the method in accordance with the invention over the known method consist in that the signal obtained by means of the invention can be used inter alia to distinguish the effects of the spin-spin relaxation time and the motion of the fluid on the signal shape in a simple manner and in that the actual spin-spin relaxation time of fluids with a constant motion and fluids with a motion which varies in time can be determined.

One version of the method in accordance with the invention is characterized in that at least one further magnetic field component is a gradient field component which is applied so that the components of the nuclear spins in a direction transversely of the constant field component are phase-shifted with respect to one another, so that they cancel the effect of one another in this direction.

Another version of the method in accordance with the invention is characterized in that the at least one further magnetic field component is generated by an r.f. electromagnetic signal so that the sum of the nuclear spins is rotated in the direction parallel to the constant field component.

Depending on the kind of fluid or the object in which the fluid is present, the use of one or both said versions may be necessary in order to obtain the desired spin resonance signal. In the method in accordance with the invention, the at least one further magnetic field component can be applied continuously, periodically, or as a combination of a continuous and a periodic magnetic field component.

Further versions yet of the method in accordance with the invention relate to the processing of the spin resonance signal obtained by artificial relaxation of the nuclear spins in order to derive therefrom the motion properties, the actual relaxation times and other properties of the fluid and the object in which it moves.

The present method is important notably for medical diagnostics and quantitative measurements of the peripheral blood circulation and the absorption of oxygen in the blood. The frequency spectrum of the spin resonance signal obtained in accordance with the invention provides information as regards the flows in the arteries whilst the spin-spin relaxation time provides information as regards the oxygen content of the venous and arterial blood. The diagnostic information is derived from a comparison of the measurement data of healthy test persons and patients, and can in both cases be represented by numbers, such as the spin-spin relaxation time and/or numerical ratios such as the frequency index which is determined from the ratio of the frequency peaks in the frequency spectra of the measurement data of the patient and the test person.

By using adjustable magnetic field gradients in one, two or three directions, resulting in a spatial selection of a part of the fluid to be measured, the method in accordance with the invention enables arterial pulsed blood flows to be distinguished from non-pulsed venous blood flows in medical applications. Using spatial selection, quantitative data can also be obtained as regards inter alia continuously flowing body fluids such as lymph, urine, etc. Generally, the method in accordance with the invention can be used on living biological objects where non-invasive measurement of the blood and fluid flows in stationary and/or moving organs and tissues is required or desired and where the method may in no case be destructive.

In addition to these bioligical applications, the method in accordance with the invention can also be used for measuring the flow of, for example agressive or viscous fluids in pipes or any arbitrarily shaped enclosures, fluids in reactor vessels, explosive fluids, etc. provided that they can be arranged in a sufficiently strong magnetic field.

Even though the method in accordance with the invention can be performed by means of the existing equipment used for performing the known method, the invention also relates to a device which is particularly suitable for producing the magnetic field components required for performing the method in accordance with the invention. All data processing operations can be readily executed on the basis of software.

BRIEF DESCRIPTION OF THE DRAWINGS

The invention will be described in detail hereinafter with reference to the accompanying drawings; therein:

FIGS. 4a and 4b show the waveform obtained by means of the known method, FIGS. 5(a-e) diagrammatically shows the pulse sequence and gradient diagram of an embodiment for performing the method in accordance with the invention.

DESCRIPTION OF THE PREFERRED EMBODIMENTS

Figure 1:
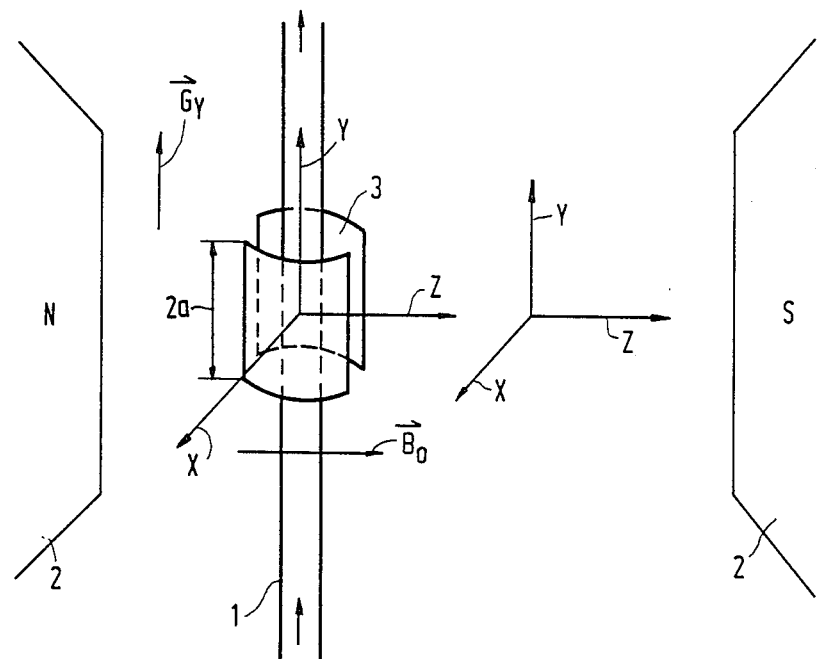
FIG. 1 is a diagrammatic representation of a measurement set-up for applying the necessary magnetic fields to a flowing fluid.

For the explanation of the known method a situation is assumed as shown in FIG. 1. The object in which the velocity of the fluid flowing therein is to be measured is in this case formed by the tube 1 which is arranged in a uniform, static magnetic field $B_o$ which is directed along the Z-axis of the laboratory coordinate system (X,Y,Z). The coordinate system can be chosen at random. The fluid is assumed to flow through the tube 1 in the direction of the arrow, i.e. in the Y-direction.

In the present example the static magnetic field $B_o$ is directed perpendicularly to the flow direction of the fluid and is generated by a magnet 2. The direction of $B_o$, however, can be chosen at random.

Figure 2:
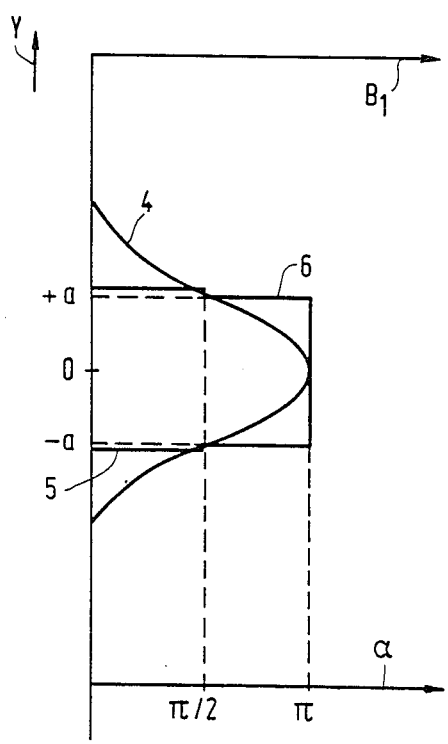
FIG. 2 shows the field strength distribution of the magnetic component generated by the r.f. pulses, FIG. 3 diagrammatically shows the effect of further time-dependent magnetic field gradients on the flowing fluid.

The tube 1 is also enclosed by an r.f. coil 3 which is symmetrically arranged with respect to the Z-axis and which is, for example of the Helmholtz type, the length 2a of said coil extending in the Y-direction. The r.f. coil 3 can generate a linearly polarized r.f. magnetic field $B_1$ perpendicularly to the static magnetic field $B_o$. The strength distribution of the r.f. magnetic field $B_1$ along the Y-axis very closely approximates a so-called gaussian profile 4, as shown in FIG. 2, when use is made of a Helmholtz coil.

The fluid to be measured is also subject to a static magnetic field gradient G in the flow direction, $G_Y=(-dB_o)_Z/dY$, where the indices denote the axis direction of the relevant quantities. For as long as no further gradient fields are present, no flow images can be derived from the signals observed.

In the state of thermal equilibrium, without r.f. magnetic field $B_1$, the macroscopic magnetization M which is equal to the sum of the individual nuclear spins in the fluid to be measured, performes a precessional motion around the location-dependent magnetic field in the Z-direction which is determined by:

$$B_Z(Y)=B_o+Y.G_Y \quad (1)$$

The precessional frequency $\omega$ is linearly dependent on the magnetic field strength and is also referred to as the Larmor frequency. In this respect:

$$\omega=\gamma.B_Z(Y) \quad (2)$$

ti where $\gamma$=gyromagnetic ratio.

The gyromagnetic ratio differs for each chemical element.

It follows from (1) and (2) that the Larmor frequency is location-dependent due to the static magnetic field gradient. Nuclei in the centre of the coil (Y=0) perform a precessional motion with $\omega_o=\gamma.B_o$, whilst $\omega<\omega_o$ for nuclei in locations where Y<0, and obviously $\omega>\omega_o$ for nuclei in locations where Y>0.

Using the r.f. coil 3, the fluid in the tube 1 is subjected to a series of n equidistant r.f. electromagnetic pulses of equal duration, thus generating the r.f. magnetic field $B_1$. Depending on the strength of $B_1$ and the duration of the individual r.f. pulses, the direction of the macroscopic magnetization M, extending along the Z-axis at the beginning of the pulse series, will be rotated away from the Z-axis through a given angle which is also referred to as the pulse angle $\alpha$. Because the r.f. magnetic field $B_1$ is not uniformly distributed along the Y-axis, the pulse angle $\alpha$ will also be a function of the location Y in the tube. Therefore:

$$\alpha(Y) = \gamma \cdot B_1(Y) \cdot t_p$$

where:
$t_p$ = pulse duration of the applied r.f. pulse.

The direction in which M is rotated depends on the direction $B_1$. In order to illustrate this phenomenon, let use consider a second coordinate system (x,y,z) which is chosen so that the z-axis extends parallel to the static magnetic field, i.e. parallel to the Z-axis of the laboratory coordinate system, the (x-y) plane rotating around this axis at an angular velocity which is equal to the Larmor frequency $\omega_o$ of the spins in the centre of the r.f. coil.

The carrier frequency of the applied r.f. pulse is chosen so that the associated magnetic field $B_1$ rotates at an angular velocity $\omega_o$, so that $B_1$ has a fixed direction in this (x,y,z) coordinate system. For the sake of simplicity the (x,y,z) coordinate system is chosen so that the direction of the x-axis coincides with the direction of $B_1$. This is also the direction along which detection takes place. The magnetization M is then rotated around the x-axis under the influence of the r.f. magnetic field $B_1$.

In order to illustrate the effect of the various magnetic fields and the flow of the fluid on the detected signal along the x-axis, we will now consider the first r.f. pulse of said pulse series which starts at the instant $t=0$, the pulse repetition time between the individual pulses being equal to T.

At the instant $t=0$, M points in the direction of the z-axis and is rotated through a given angle around the x-axis by the first pulse. During the period $T-t_p$, i.e. until the beginning of the next pulse, the excited spins moving in the tube 1 fan out symmetrically around the y-axis and incur a given phase shift in the (x,y) plane, because these spins propagate in a non-uniform magnetic field.

The phase shift $\phi(t)$ incurred by the spins equals:

$$\phi(t) = \int_0^t \omega(t)dt \quad t_p \leq t \leq T - t_p$$

where:

$$\omega(t) = \gamma B(t) = \gamma[B(t=0) + G_y Y(t)]$$
$$\omega(t) = \gamma[B(t=0) + G_Y \{Y(0) + v \cdot t\}]$$

and
v = flow velocity of the fluid
Y(0) = position of the spins at $t=0$.
This results in a phase shift of the net magnetization in the (x,y) plane and hence in a magnetization component along the x-axis, i.e. the detection direction.

In the (x,y) plane the nuclei are subject not only to the non-uniform field caused by the magnetic field gradient but also to local inhomogeneities which are caused by chemical shifts and dipole interactions in the fluid; they are also subject to inhomogeneities in the static magnetic field $B_o$ itself due to faults in the magnet 2. The static magnetic field $B_o$, however, is assumed to be so large that these inhomogeneities may be ignored.

It will be apparent that in the case of an non-moving fluid the diverging spins incur opposed phase shifts with respect to the centre of the coil due to the static magnetic field gradient, which shifts eliminate one another. Therefore, no resultant component of the magnetization will appear along the x-axis so that no signal can be detected. Consequently, stationary and moving fluids, can be effectively discriminated.

The magnetic field strength distribution of the r.f. coil 3 is chosen so that the spins in the centre of the coil are rotated 180° ($\pi$ rad) around the x-axis with respect to the magnetic field in the z-direction and through 90° ($\pi/2$ rad) at the ends $(-a, a)$, see FIG. 2. An approximation of the gaussian curve 4 by two rectangular curves 5, 6 reveals that spins which enter the coil at $Y = -a$ are rotated through substantially 90° and are subsequently exposed to one or more r.f. pulses which cause a rotation of substantially 180° at the area $-a < Y < a$, subject to the condition that the nuclei are still present in the coil at the instant at which these 180° pulses are applied, so if:

$$2a/v > T - t_p$$

The first 90° r.f. pulses causes a so-called free induction decay (FID), which means the signal occurring along the y-axis due to the mutual divergence of the nuclear spins after application of the r.f. pulse. The 180° pulses whereto the diverging spins are subsequently subjected invert the instantaneous direction, but the relaxation sense thereof is not changed. For the magnetization component in the detection direction, in this case the x-direction, this means that it alternately moves in opposite directions around the x-axis. The maximum in the detected signal, arising when the magnetization component passes through the x-axis, i.e. is parallel thereto, is referred to as a spin echo. In practice various pulse series consisting of 90° and 180° pulses are known. This known method of measuring flow properties of fluids is also known as the repetitive pulse method (RP method).

Due to the fanning out of the spins, the intensity of the magnetization in the (x-y) plane decreases exponentially as a function of the time constant $T_2$ in a uniform magnetic field; this is said spin-spin relaxation time. The return of the magnetization to the z-direction is determined by said spin lattice relaxation time $T_1$, where $T_2 \leq T_1$. Relaxation processes have a crucial function in nuclear magnetic resonance. For more information in this respect reference is made to "Pulse and Fourier Transform NMR. Introduction to the Theory and Methods", by T. C. Farrar and E. D. Becker, published by Academic Press 1971.

Because in a moving fluid non-excited spins flow into the coil at the end $y = -a$ and excited spins leave the coil at the other end $y = a$ so that they are lost to the detection, in the course of time the detected signal reaches a steady final value where all spins in the coil have the same "history".

Generally three types of flows are distinguished:

1. laminar flow;
2. turbulent flow; and
3. "plug" flow, each flow type being characterized by its own spatial flow profile. In the case of a laminar flow the flow velocity is highest at the centre of the fluid and decreases as a square-law function in the radial direction. This type of flow can be observed, for example in biological systems where the flow is comparatively slow, for example in the veins of humans and animals. In the case of a turbulent flow the velocity decreases far less rapidly, viewed in the radial direction, than in the case of a laminar flow. Turbulent flow is to be expected when high flow velocities are reached, for example in the aorta and near branches in the vascular system. "Plug" flow is a type of flow where the velocity of the fluid is constant in the radial direction and is observed in, for example moving, tissues in which the fluid itself has no movement component, such as biological systems in moving objects.

The detected spin resonance signal of a fluid in a static magnetic field with a gradient field component in the movement direction and excited by a series of r.f. electromagnetic pulses is a mean value of the contributions of spins at different locations in the fluid and does not contain information for inter alia determining the spatial distribution of the movement properties of the fluid.

In order to enable determination of the spatial movement profile of the fluid it is necessary to subject the fluid, in addition to the static magnetic field gradient in the movement direction and the magnetic field $B_1$ generated by the r.f. pulses, to one or more mutually orthogonal time-dependent magnetic field gradients perpendicularly to the flow direction, i.e.

$$G_Z(t) = G_Z \sin \omega_m t \text{ and/or}$$

$$G_X(t) = G_X \sin (\omega_m t + \Psi)$$

where:
$G_Z$ = maximum magnetic field gradient in Z-direction
$G_X$ = maximum magnetic field gradient in X-direction
$\omega_m$ = modulation frequency, and
$\Psi$ = phase angle.

These gradients are also referred to as "modulated" magnetic field gradients. The indices again denote the axis direction of the relevant quantities which are applied to the fluid across the entire length $2a$ of the r.f. coil 3 (FIG. 1). Both time-dependent gradient fields are synchronized with the r.f. pulse series via $\omega_m = 2\pi/nT$.

For the application of these magnetic field gradients use is made of so-called gradient field coils which may consist of pairs of coils in the X-, the Y- and the Z-direction in practical embodiments of measurement devices.

Due to the mutually cancelling phase shifts incurred by the spins in the fluid under the influence of such a time-dependent magnetic field gradient, a so-called "zero" plane arises in the fluid, the spins incurring an opposed phase shift on both sides thereof. The "zero" planes 7, 8 shown in FIG. 3 correspond to $G_Z(t)$ and $G_X(t)$, respectively. The position of these "zero" planes is determined by the coordinates $X_0$ and $Z_0$ which are situated on the X-axis and the Z-axis, respectively. The coordinates $X_0$ and $Z_0$ depend on the shape of the gradient coils and the ratio of the currents through a coil pair.

Figure 3:
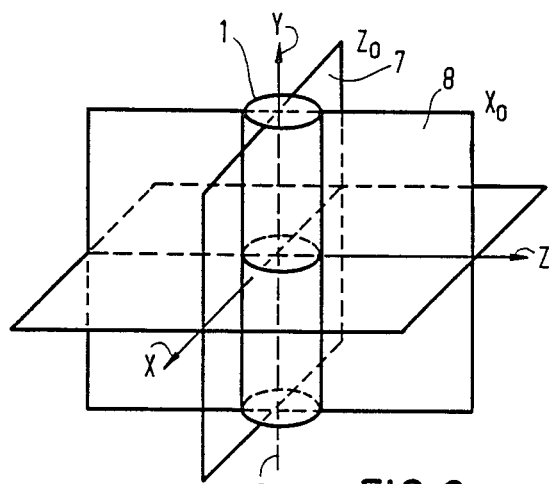

In the situation shown in FIG. 3 the phase angle $\Psi = 90°$ so that a rotating "zero" plane is obtained. The line 9 about which the zero plane rotates is referred to as the "sensitive line". In the case of only one gradient field, the term "sensitive plane" is used. The flow velocity of the fluid can be determined along the "sensitive line" or in the "sensitive plane". The position of the sensitive line can be shifted by variation of the current ratio in the gradient coils, so that the flow profile can be line-wise determined throughout the entire tube 1. By application of a further modulated magnetic field gradient in the flow direction (Y) or so-called "selective" r.f. pulses, a volume element or "voxel" can be selected in which the flow properties can be determined. For further information concerning the measurement of spatially distributed motion profiles reference is made to "A Novel NMR Method for Spatially Resolved Flow Measurements" by H. van As et al., "Journal of Magnetic Resonance", 62, 1985, pp. 511–517 and "NMR imaging in Biomedicine" by P. Mansfield and P. G. Morris, Academic Press, 1982.

As has already been stated, the magnetization component is detected along the x-axis for which use can be made of the same r.f. coil as used for applying the r.f. pulses to the fluid to be measured. The response signal $S(t)$ is obtained from the sampling of the net magnetization component along the x-axis between the r.f. pulses or by integration thereof during a period of time equal to a multiple of the pulse repetition time T.

The pulse angle $\alpha$ wherethrough the magnetization M is rotated about the x-axis can vary from approximately 30° to approximately 200° without the essence of the measurement being affected thereby. The magnitude of the pulse angle has an effect mainly on the intensity of the detected signal and hardly any effect on the shape thereof.

Viewed in time, the envelope of the total signal $S(t)$ detected along the x-axis after a series of r.f. pulses can assume, mainly two different shapes as shown in the FIGS. 4a and b, depending on the phase development during the staying time of the spins in the measurement coil, the references a to h referred to different flow velocities, for which:

$$v_a < v_b < \ldots < v_h.$$

Figure 4B:
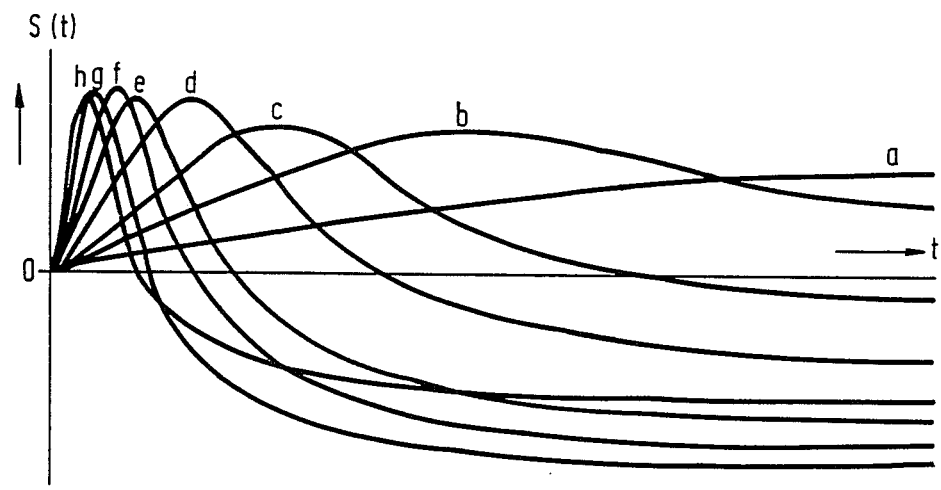
Figure 4B:
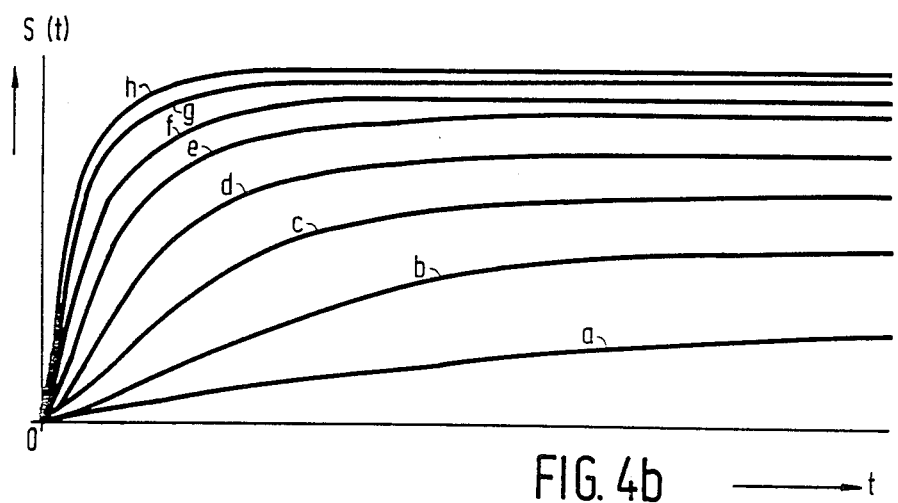

When the flow conditions exert such an effect that the fanned out spins incur a phase shift in excess of 90°, the signal $S(t)$ will inhibit one or more local extreme values as indicated in FIG. 4a. When the phase shift of the spins is smaller than 90°, the signal $S(t)$ of the detector tends to an extreme value $S_e$ in the steady state as indicated in FIG. 4b. The units along the vertical axis are then arbitrary.

In the case of a continuous flow which does not vary in time, the following quantities can be derived from the signals obtained:

In circumstances where the signal has one or more local extreme values (maximum and/or minimum values):

(a) the linear flow velocity v (m/s) from the position $t_{max}$ of the extreme value or values;

(b) the volumetric flow velocity $Q(m^3/s)$ from the initial slope of $S(t)$ for $t = 0$: $(dS/dt)_t = 0$.

In circumstances where the final level $S_e$ of the signal is the extreme value:

(a) the volumetric flow velocity Q from the initial slope of $S(t)$ for $t = 0$: $(dS/dt)_t = 0$;

(b) the linear and the volumetric flow velocity v and Q from the final level $S_e$.

For example, for many medical applications it suffices to determine the linear flow velocity v along a line in the object perpendicularly to a cross-section of, for example a blood vessel. The volumetric flow velocity Q is then given by:

$$Q = v \cdot A$$

where:

A = cross-section of the blood vessel.

In the case of a pulsating flow of the fluid, as shown in FIG. 7, the mean volumetric flow velocity $\overline{Q}$ and the volumetric flow velocity Q(t) can be determined from the signals S(t) at any arbitrary instant during the pulsating flow.

After calibration, each of the measured quantities can be measured in an absolute sense. Calibration is performed by measuring in said known manner the final level $S_e$ of the signal obtained as a result of the flow through an inert tube and by volumetrically determining the conducted amount of fluid during the same experiment.

As has already stated in the preamble, the calibration curves for the relation between v and $t_{max}$ and between $S_e$ and Q, v are dependent on the flow profile of the fluid. These calibration curves are also determined to a high degree of said spin-spin and spin lattice relaxation times, being $T_2$ and $T_1$, respectively. Therefore, the calibration should be performed for different values of $T_2$. As has already been stated, notably $T_2$ is of a fluid with a flow which varies, for example a pulsating flow, can only be reliably measured by means of the known method if the highest frequency of the frequency spectrum of the motion which varies in time is lower than $(2\pi/T_2)^{-1}$. For blood, $T_2$ amounts to approximately from 0.2 to 0.3 s in the case of a magnetic field strength of approximately 0.5 Tesla, so that frequencies in excess of approximately 1 Hz are not reliably measured.

As will be apparent from the foregoing, the known method is only suitable for performing accurate measurements on chemically pure fluids whose relaxation time $T_2$ is known and invariable. Measurements performed on blood flows in, for example, the human body per definition suffer from a comparatively great inaccuracy due to the fact that this $T_2$ can vary strongly, as has already been stated in the preamble, for example due to the absorption of oxygen by the blood, so that it is actually unknown during the execution of the measurement.

It is the object of the invention to eliminate the effect of the actual relaxation times of the fluid on the measurement results by causing the excited nuclear spins to relax in a manner imposed by the measurement. By influencing the manner in which the components of the excited nuclear spins fan out in the (x,y) plane, the observed spin-spin relaxation time $T_2$ can be artificially fixed, regardless of the nature and the properties of the fluid being measured.

In this respect one can also speak of an artificial effective relaxation time $T_{2,eff}$, where $T_{2,eff} < T_2$. The value of $T_{2,eff}$ now depends on the manner in which the excited nuclear spins are forced to fan out. In relation to the known RP method the method in accordance with the invention could also be called the "Modified RP method" or "Modified Repetitive Pulse (MRP) Method".

In accordance with the invention, the fluid is subjected to a further magnetic field which may consist of one or more magnetic field components. These may be gradient field components as well as r.f. field components or combinations thereof. As has already been described with reference to the r.f. magnetic field $B_1$, r.f. magnetic field components can be used to rotate the magnetization about the x-axis so that it disappears from the (x,y) plane. Using suitably applied gradient field components, the magnetization of the components of the nuclear spins can be dephased with respect to one another at different locations in the (x,y) plane. This further magnetic field can be applied continuously or pulsed periodically, as a combination of a continuous gradient field component and a pulsed r.f. magnetic field component or vice versa, etc. This further magnetic field could be referred to as a "spoil" field. In the case of pulsed magnetic field components one could use the term "spoil" pulses.

Figure 5:
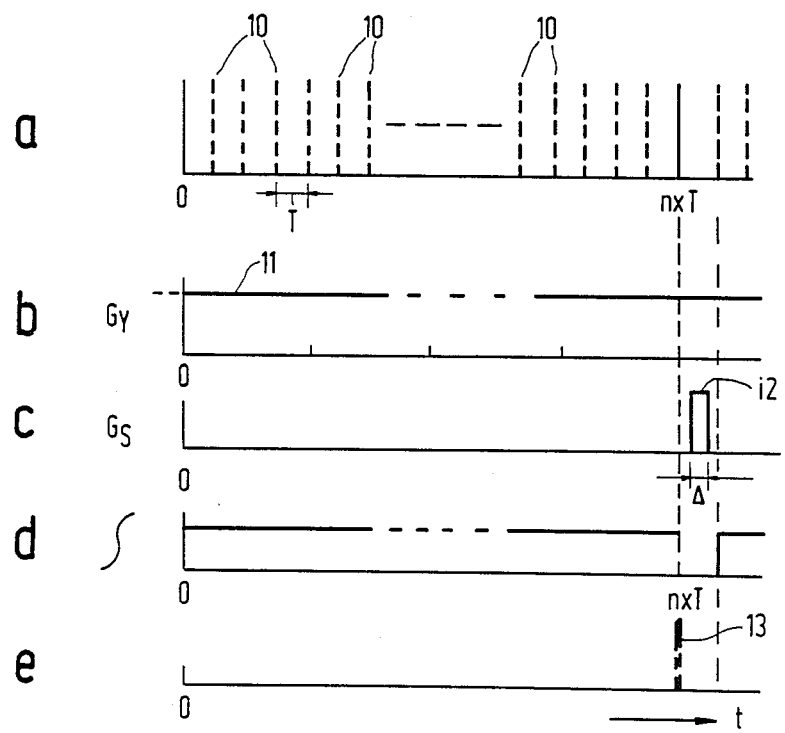

FIG. 5 diagrammatically shows the application in time of a magnetic field gradient spoil pulse in a direction perpendicular to the flow direction of the fluid shown in FIG. 1. FIG. 5a shows a series of r.f. pulses 10, each of which corresponds to a pulse angle α. The individual pulses are represented by broken lines for the sake of simplicity; in practice they have a given duration $t_p$. FIG. 5b shows the static magnetic field gradient 11 in the flow direction which, of course, is constant in time. The responses caused by the r.f. pulses are detected in integrated form during a period nT as shown in FIG. 5d. The integrated signal thus obtained from n r.f. pulses is sampled at the end of the integration period nT as denoted by the reference numeral 13 in FIG. 5e. After the sampling of the signal, a magnetic field gradient spoil pulse 12 having the intensity $G_s$ is applied perpendicularly to the flow direction for approximately a period Δ. This magnetic field gradient spoil pulse causes dephasing of the spins in the (x,y) plane, so that the magnetization in this plane is cancelled, which corresponds to an artificial reduction of the spin-spin relaxation time $T_2$. After termination of the spoil pulse $G_s$, the integration of the next series of n r.f. pulses commences, resulting in the signal S(t). The artificial spin-spin relaxation time $T_{2,eff}$ is determined by the product $\Delta \cdot G_s$.

For measuring, for example the local blood flow in a finger of a human hand in this manner, the following parameter values can be used:

r.f. pulse angle: 30°–200°
T: 0.5–2.0 ms
$G_y$: $10^{-3}$ T/m
$G_y \cdot T \sim 0.5 \cdot 10^{-6}$ Ts/m
n.T ~ 20 ms (integration time)
$\Delta \cdot G_s \sim 5$–$30 \cdot 10^{-6}$ Ts/m.

The spoil pulse can also be applied at other instants during the r.f. pulse series or a plurality of spoil pulses can be applied in succession. Instead of a magnetic field gradient spoil pulse $G_s$, an r.f. spoil pulse can also be used in FIG. 5. It will be apparent that the method of applying a spoil pulse as illustrated in FIG. 5 can also be used in combination with further time-dependent magnetic field gradients such as is the case with the so-called sensitive line, sensitive plane or voxel method. The intensity of the magnetic field gradients $G_Z$, $G_X$ which is decisive for the spatial resolution amounts to approximately 5–10 $10^{-3}$ T/m during the aforesaid measurement, when $\omega_m = 2\pi/nT \sim 2\pi \cdot 50$ rad/s. In accordance with the ideal of the invention, instead of or in combination with a separate spoil magnetic field, use can alternatively be made of one or both gradient field components $G_Z$ and $G_X$ with a suitable strength.

As a result of the use of spoil pulses, the calibration curve for the relationship between Q and Se during the determination of the quantities in accordance with the method of the invention will no longer be dependent on v and the actual spin-spin relaxation time $T_2$ of the fluid, but rather on $T_{2,eff}$.

As a result of this effective shorter spin-spin relaxation time, in comparison with the prior art method the method in accordance with the invention enables the measurement of movement which vary more quickly in time. For example, for pulsating flows it has been found that the volumetric flow velocity Q(t) which varies in time can be reliably measured for time-varying flows whose highest frequency in the frequency spectrum is lower than $(2\pi T_{2,eff})^{-1}$. After the execution of the calibration of the volumetric velocity Q versus Se,Q(t) can be derived at any instant from the detected signal S(t) in the circumstances in which the final level $S_e$ of the signal is the extreme value.

In addition to the important advantage that the method in accordance with the invention enables reliable measurement within broad limits of the flow properties of fluids with a movement which varies in time, for example pulsating flows, it is also possible to determine the actual spin-spin relaxation time $T_2$ of the fluid directly from the measurement signal. This is not possible by means of the known RP method.

It can be demonstrated that for a fluid with a movement which does not vary in time the effective spin-spin relaxation time $T_{2,eff}$ can be derived from the ratio of the signal measured in accordance with the invention, the MRP method, to the initial slope thereof, i.e. from $S_e$(MRP)/$(dS/dt)_{t=0}$.

It can also be demonstrated that $T_{2,eff}$ can also be determined from the final level $S_e$ of S(t), measured in accordance with the invention on a fluid which moves at a known velocity, where $T_2 > T_{2,eff}$. This requires a calibration curve for the relationship between $S_e$ and $T_2$, obtained by means of the known RP method, for the given velocity under the given measurement circumstances.

The frequency spectrum of Q(t) or S(t) can be determined in known manner by way of Fourier transformation, Laplace transformation or a similar mathematical operation. For digital processing the so-called Fast Fourier technique can be used.

The frequency spectrum $F_g(\gamma)$ of S(t), determined by means of the method in accordance with the invention, can be corrected, because $T_{2,eff}$ is known, so as to obtain the actual frequency spectrum $F(\gamma)$ wherefrom subsequently the actual movement variation can be determined, for example the actual pulse shape $Q_w(t)$ in the case of a pulsed flow.

The actual spin-spin relaxation time $T_2$ of the moving fluid can thus be calculated from the measurement results in the following manners:

(a) for continuous (smooth) movement: from the ratio of $S_e$, obtained in accordance with the known RP method, and $S_e$ obtained in accordance with the method of the invention, the MRP method, i.e. $S_e$(RP)/$S_e$(MRP) or from the ratio $S_e$(RP)/$(ds/dt)_{t=0}$;

(b) for a movement which varies in time: from the ratio of the standardized amplitudes $A_n$ of the higher harmonics $F(\gamma)$ or $F_g(\gamma)$ obtained by means of the MRP method in accordance with the invention and $F(\gamma)$ obtained by means of the known RP method, $A_n(T_{2,eff};$ MRP)/$A_n(T_2;RP)$, where n = 1, 2, 3 and $A_n$ is standardized to $A_1 = 1$ or $A_o = 1$ (fundamental harmonic).

In the situation specified sub (b) $T_2$ follows from:

$$(T_2)^2 = \frac{b - (a)^2}{(2\pi v a)^2 - b(2\pi n v)^2}$$

where:

$a = A_n(T_{2,eff};MRP)/A_n(T_2;RP)$ with $A_n$ standardized to $A_1$, and $b = (1 + 2\pi\gamma T_{2,eff})/(+ 2\pi n\gamma T_{2,eff})$.

It can be demonstrated that $T_2$ is proportional to the inverse of the 3 dB breakpoint of the curve: $W(\gamma) = F_g(\gamma)/F(\gamma)$ determined by means of the method in accordance with the invention.

Figure 6A:
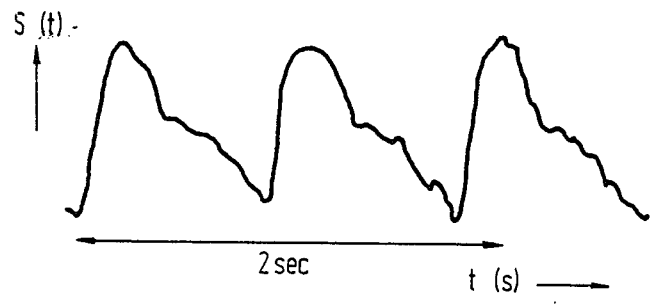
FIG. 6a shows the variation of the spin resonance signal measured by means of the known method and FIG. 6b shows the frequency spectrum thereof for a pulsating local blood flow in a finger of the human hand.
Figure 6B:
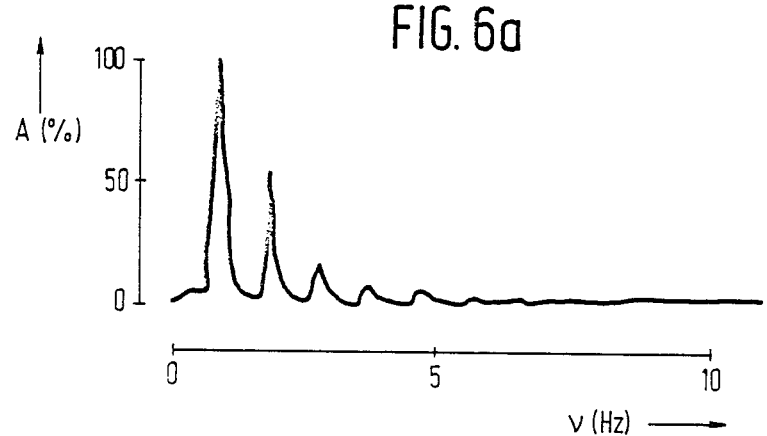

FIG. 6 shows a typical variation of the signal S(t) and the frequency spectrum $F(\gamma)$ of the pulsating part of a local blood flow in a finger of a human hand, measured by means of the known method. In the frequency spectrum the various characteristic frequencies of the blood flow and their relative amplitudes such as they occur in the signal S(t) can be clearly recognized.

An example of an application for indicating the properties of a non-continuously flowing fluid is formed by the so-called frequency index i. The signal shape S(t) is then recorded in by means of the method in accordance with the invention, after which the frequency spectrum $F_g(\gamma)$ is determined. Subsequently, the frequency index i is determined from the ratio R of the highest peak but one and the highest peak in the measured frequency spectrum, and a similar ratio for a standard reference $R_r$, where $i = R/R_r$. The ratio of the peaks of the standard reference may be determined in advance. Q(t), $Q\omega(t)$, $F_g(\gamma)$ and $F(\gamma)$ are available for pulse shape analyses as known inter alia from ultrasonar doppler flow measurements, such as "pulsatilition index (frequency index), Argend diagram" etc. See inter alia Cliffors, Baird in "Blood flow measurements in man", R. T. Mathie ed., Chapter 17, Castle House Publ. Ltd., London 1982.

Figure 7A:
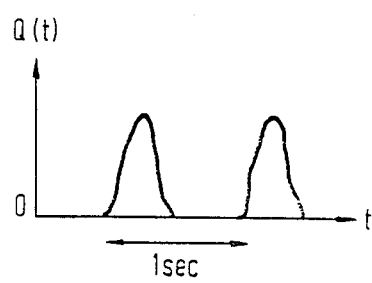
FIG. 7a shows a pulsating flow signal measured in a test set-up by means of a differential pressure flow meter and FIG. 7b shows the spin resonance signal thereof measured by means of the known method.
Figure 7B:
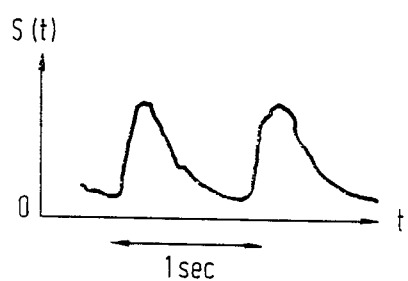

In FIG. 7 a pulsating flow signal has been measured in a test set-up by means of a differential pressure flow meter (FIG. 7a) and by means of the spin resonance technique (FIG. 7b). For Q(t) = constant, in this case Q(t) = 0[v(t) = 0], the NMR signal S(t) decreases according to $e^{-t/T_2}$. The $T_2$ relaxation time can also be determined from this part of the signal S(t). The part for which Q(t) = constant can be determined by means of the MRP method.

For a further theoretical elaboration as regards the determination of $T_2$ from the measurements performed on a moving fluid reference is made to the non-published report of the doctoral study by J. E. M. Snaar "Gepulseerde Stromingsmetingen met de "Repetitive pulse"—Methode aan Modelsystemen", Landbouwuniversiteit Wageningen, October 1986. This report had not been made public prior to the filing date of the present Patent Application.

Figure 8:
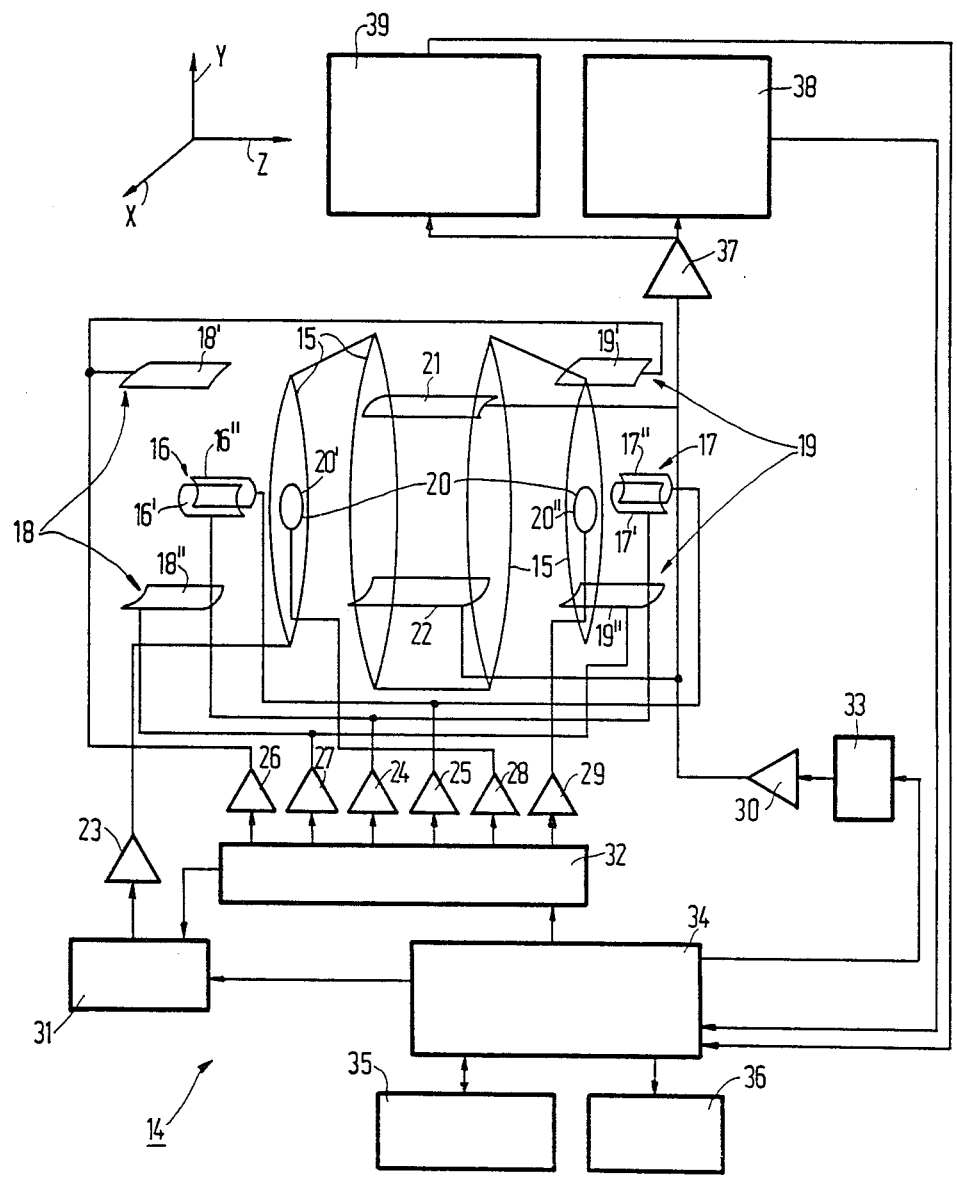
FIG. 8 diagrammatically shows a preferred embodiment of a device for performing the method in accordance with the invention.

Devices for performing nuclear magnetic resonance (NMR) measurements on moving fluids or for making images are known from the state of the art; for example, see European Patent Application EP-A-0106472. Hereinafter a preferred embodiment of a device will be described with reference to FIG. 8; using this device, the at least one further magnetic field component required for the imposed relaxation of the excited nuclear spins can be generated by an r.f. field component and/or a gradient field component.

The device comprises a first coil system, consisting of a series connection of coils 15, whereby a constant, uniform magnetic field can be generated in the Z-direction of the laboratory coordinate system, coils 16, 17 for forming a magnetic field gradient component in the X-direction, coils 18, 19 for forming a magnetic field gradient component in the Y-direction, and a coil 20 for forming a magnetic field gradient component in the Z-direction.

The device also comprises a second coil system 21, 22 whereby the object to be examined can be subjected to r.f. magnetic field components perpendicularly to the direction of the magnetic field generated by the first coils 15 and whereby r.f. magnetic fields originating from the excited nuclear spins of the fluid in the object to be examined can be detected in directions other than the Z-direction. It will be apparent that instead of one coil system 22 for applying as well as detecting r.f. magnetic fields use can alternatively be made of separate coils for the detection of the r.f. magnetic field originating from the excited nuclear spins.

The various coils 15; 16, 17; 18,19; 20; 21 and 22 are energized via respective drivers 23; 24, 25; 26, 27; 28, 29 and 30 which are connected to control circuits 31, 32 and 33 as shown in the Figure. These control circuits can be constructed in various ways and are known from the state of the art.

Each of the gradient coils 16, 17, 18, 19 and 20 consists of a coil pair which is symmetrically arranged with respect to the longitunal axis of the device 14 in the Z-direction. Contrary to the known NMR devices, the separate coils 16', 16", 17', 17", 18', 18", 19', 19", 20' and 20" of each coil pair 16, 17, 18, 19 and 20, respectively, can be separately driven. In the embodiment shown the correspondingly situated coils 16', 17' are driven by the driver 24, the coils 16", 17" by the driver 25, the coils 18', 19' by the driver 26, and the coils 18", 19" by the driver 27. Using a device having such a construction, the magnetic field gradients necessary for the relaxation of the nuclear spins in accordance with the method of the invention can be generated in any desired direction.

The control circuits 31, 32 and 33 are controlled by a central processing and control unit 34 whose inputs and outputs are connected to peripheral apparatus 35 in order to issue instructions to the unit 34 for executing the measurement process. A display device 36 is connected to the unit 34.

The NMR signals detected by the coils 21, 22 are applied, via an amplifier 37, to a signal processing circuit 38 and a field and error signal measuring device 39. The signal processing circuit 38 is suitable for performing a suitable calibration and correction of the signals, the detected signals being converted into a suitable shape for processing by the central processing and control unit 34, after which they are applied, for example to the display device 36 for the formation of an image of the detected signal.

Even though the signal processing system 38 is shown as a separate unit, it can of course be included in the central processing and control unit 34.

It will be apparent that the invention is not restricted to the described applications and the embodiments shown in the Figures and that many modifications and additions are feasible without departing from the scope of the invention.

What is claimed is:

1. A method of deriving a spin resonance signal from a moving fluid which is subjected to a magnetic field consisting of a constant field component, one or more gradient field components of which at least one extends in the direction of motion of the fluid, and an r.f. field component generated by r.f. electromagnetic signals, the r.f. field component being perpendicular to the constant field component and exciting the nuclear spins of the fluid; such method comprising the steps of:

subjecting the fluid to at least one further gradient field component which produces relative phase shifts of components of the excited nuclear spins in a direction transversely to the constant field component, such phase shifts mutually cancelling the spin excitations in said transverse direction so they are caused to relax as imposed by said further gradient field component; and detecting and measuring magnetic resonance signals obtained from said fluid in response to said nuclear spin excitation.

2. A method as claimed in claim 1, wherein the at least one further magnetic field component is continuously applied.

3. A method as claimed in claim 1, characterized in that the at least one further magnetic field component is periodically applied.

4. A method as claimed in claim 2, wherein the at least one further magnetic field component consists of a combination of a continuously applied magnetic field and a periodically applied magnetic field.

5. A method as claimed in claim 3, wherein the at least one further periodically applied magnetic field component is pulse-shaped.

6. A method as claimed in claim 3, wherein the at least one further periodic magnetic field component is applied after a predetermined number of r.f. electromagnetic pulses whereby the nuclear spins are excited.

7. A method as claimed in claim 3, wherein the resonance signals obtained by means of the r.f. electromagnetic pulses are detected in an integrated manner during a predetermined period, the at least one further periodic magnetic field component being applied at the end of each integration period.

8. A method as claimed in claim 1, wherein for a fluid having a movement velocity which varies in time the spin-spin relaxation time ($T_2$) is determined from the ratio of amplitudes of the higher harmonics of the frequency spectra of the measured signal and a signal which is measured without further magnetic field component.

9. A method as claimed in claim 1, wherein for a fluid having a movement velocity which varies in time the spin-spin relaxation time ($T_2$) is determined from the inverse of the 3 dB breakpoint of the ratio of the frequency spectra of the measured signal and a signal which is measured without further magnetic field component.

10. A method as claimed in claim 1, wherein a frequency index i which characterizes a moving fluid is determined from the ratio of the highest peak but one and the highest peak of the frequency spectrum of the measured signal (R) and of a standard reference ($R_r$).

11. A method as claimed in claim 1, wherein for a fluid having a movement velocity which does not vary in time, the imposed spin-spin relaxation time ($T_{2,eff}$) is determined from the ratio of the final level ($S_e$) of the measured signal and the initial slope thereof $((dS/dT)_{t=0})$.

12. A method as claimed in claim 1, wherein for a fluid having a known movement velocity the imposed spin-spin relaxation time ($T_{2,eff}$) is determined from the final level ($S_e$) of the measured signal, on the basis of a calibration curve of the relation between this final level ($S_e$) and the spin-spin relaxation time ($T_2$).

13. A method as claimed in claim 1, wherein for a fluid having a movement velocity which does not vary in time the spin-spin relaxation time ($T_2$) is determined from the ratio of the final levels of a signal measured without further magnetic field component and the measured signal.

14. A method as claimed in claim 1, wherein the frequency spectrum of the movement of the fluid is derived from the frequency spectrum of the measured signal on the basis of the imposed spin-spin relaxation time ($T_{2,eff}$).

15. A method as claimed in claim 14, wherein the movement variation of the fluid in time is derived from the derived frequency spectrum.

16. A device for deriving a spin resonance signal from a moving fluid, which device includes means for subjecting said fluid to a magnetic field consisting of a constant field component, at least one gradient field component in the direction of motion of said fluid, and an r.f. field component perpendicular to the constant field component, said r.f. field component exciting nuclear spins of said fluid; characterized in that said device further comprises means including at least one pair of coils for establishing a further gradient field component which produces relative phase shifts for components of the excited nuclear spins in a direction transversely to said constant field component, such phase shifts mutually cancelling the spin excitations in said transverse direction so they are caused to relax as imposed by said further gradient field component; and means for detecting and measuring magnetic resonance signals obtained from said fluid in response to said nuclear spin excitation.

17. A device as claimed in claim 16, further comprising means for separately driving each coil of said at least one pair of coils.

18. A device as claimed in claim 16, wherein said means for establishing said further gradient field component consists of a plurality of spatially shifted pairs of coils, the correspondingly situated coils (16', 17'; 16", 17"; 18', 19'; 18", 19") in each of said pairs of coils (16, 17, 18, 19) being interconnected together.

19. A method of deriving a spin resonance signal from a moving fluid which is subjected to a magnetic field consisting of a constant field component, one or more gradient field components, at least one of which extends in the direction of motion of the fluid, and magnetic field component which is generated by r.f. electromagnetic signals perpendicularly to the constant field component in order to excite the nuclear spins of the fluid, comprising the steps of subjecting the fluid to at least one further magnetic field component so that the excited nuclear spins relax in a manner imposed by said at least one further magnetic field component and detecting and measuring magnetic resonance signals obtained by the at least one further magnetic field component.

* * * * *